US009931095B2

(12) United States Patent
Pack et al.

(10) Patent No.: US 9,931,095 B2
(45) Date of Patent: Apr. 3, 2018

(54) METHOD FOR SEGMENTING SMALL FEATURES IN AN IMAGE VOLUME

(71) Applicant: General Electric Company, Schenectady, NY (US)

(72) Inventors: Jed Douglas Pack, Niskayuna, NY (US); Brian Edward Nett, Wauwatosa, WI (US); Sathish Ramani, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 56 days.

(21) Appl. No.: 15/085,577

(22) Filed: Mar. 30, 2016

(65) Prior Publication Data

US 2017/0281112 A1 Oct. 5, 2017

(51) Int. Cl.
*G06T 11/00* (2006.01)
*G06T 3/00* (2006.01)
*G06T 5/20* (2006.01)
*G06T 7/00* (2017.01)
*G06T 7/20* (2017.01)
*A61B 6/03* (2006.01)
(Continued)

(52) U.S. Cl.
CPC ............ *A61B 6/5264* (2013.01); *A61B 6/032* (2013.01); *G06T 3/0093* (2013.01); *G06T 5/002* (2013.01); *G06T 5/20* (2013.01); *G06T 7/0012* (2013.01); *G06T 7/0081* (2013.01); *G06T 7/2033* (2013.01); *G06T 11/005* (2013.01); *G06T 2207/10081* (2013.01)

(58) Field of Classification Search
CPC ..... A61B 6/5264; A61B 6/032; G06T 3/0093; G06T 5/002; G06T 5/20; G06T 7/0012; G06T 7/0081; G06T 7/2033; G06T 11/005; G06T 2207/10081
See application file for complete search history.

(56) References Cited

U.S. PATENT DOCUMENTS 6,532,380 B1   3/2003   Close et al.
6,888,916 B2   5/2005   Launay et al.
(Continued)

FOREIGN PATENT DOCUMENTS

WO   2015/092612 A1   6/2015

OTHER PUBLICATIONS

Mostapha et al. "A Novel Framework for the Segmentation of MR Infant Brain Images." IEEE International Conference on Image Processing, Sep. 27, 2015, pp. 88-92.*
(Continued)

*Primary Examiner* — Jon Chang
(74) *Attorney, Agent, or Firm* — Pabitra K. Chakrabarti

(57) ABSTRACT

According to some embodiments, system and methods are provided comprising determining one or more image locations at which motion occurred within an image volume of an object containing movable anatomical features prior to segmenting the movable anatomical features; estimating motion at each of the one or more image locations; correcting one or more motion artifacts in the image volume at each of the one or more image locations, where motion was estimated resulting in the generation of a final motion compensated image; and segmenting one or more features of interest in the final motion compensated image. Numerous other aspects are provided.

18 Claims, 7 Drawing Sheets

(51) Int. Cl.
*A61B 6/00* (2006.01)
*G06T 5/00* (2006.01)

(56) References Cited

U.S. PATENT DOCUMENTS

| | | | |
|---|---|---|---|
| 8,224,056 | B2 | 7/2012 | Pack et al. |
| 8,849,005 | B2 | 9/2014 | Sundar et al. |
| 2007/0116332 | A1 | 5/2007 | Cai et al. |
| 2007/0258643 | A1* | 11/2007 | Lotjonen ............... G06K 9/00 382/173 |
| 2009/0093711 | A1* | 4/2009 | Hermosillo Valadez ............... A61B 5/055 600/420 |
| 2011/0060755 | A1 | 3/2011 | Mollus et al. |
| 2011/0206247 | A1 | 8/2011 | Dachille et al. |
| 2013/0039557 | A1* | 2/2013 | Wei ............... G06K 9/00214 382/131 |
| 2014/0268168 | A1 | 9/2014 | Feldman et al. |
| 2014/0362970 | A1 | 12/2014 | Launay et al. |
| 2015/0063534 | A1 | 3/2015 | Allmendinger et al. |

OTHER PUBLICATIONS

Carvalho et al. "Lumen Segmentation and Motion Estimation in B-Mode and Contrast-Enhanced Ultrasound Images of the Carotid Artery in Patients With Atherosclerotic Plaque." IEEE Transactions on Medical Imaging, vol. 34, No. 4, Apr. 2015, pp. 983-993.*
Shechter, Guy et al. "Three-Dimensional Motion Tracking of Coronary Arteries in Biplane Cineangiograms", IEEE Trans Med Imaging, Author Manuscript, Apr. 2003, vol. 22, No. 4, DOI: 10.1109/TMI.2003.809090, (pp. 493-503, 26 total pages).

* cited by examiner

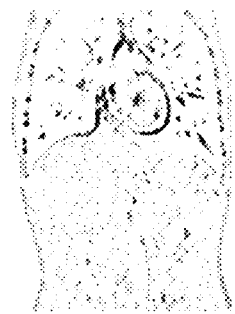
FIG. 6A
FIG. 6B
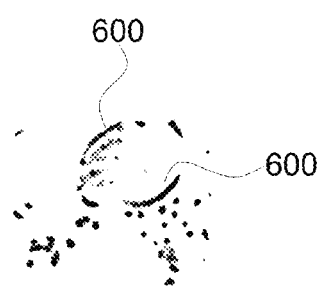
FIG. 6C
FIG. 6D

METHOD FOR SEGMENTING SMALL FEATURES IN AN IMAGE VOLUME

BACKGROUND

Computed Tomography (CT) is a non-invasive imaging technique. One of the challenges in CT is that small features may be distorted or obscured due to the fact that these features may move during data acquisition. Since most image reconstruction techniques do not account for this motion, the resulting image includes image artifacts. These image artifacts may often severely distort small features, making segmentation tasks (e.g., vessel detection and vessel tracking, identification of lung nodules, etc.) challenging.

Therefore, it would be desirable to provide a system and method that accounts and compensates for the motion-induced artifacts that occur during image acquisition.

BRIEF DESCRIPTION

According to some embodiments, a method includes determining one or more image locations at which motion occurred within an image volume of a movable anatomical feature prior to segmenting the movable anatomical feature; estimating motion at each of the one or more image locations; correcting one or more motion artifacts in the image volume at each of the one or more image locations where motion was estimated, resulting in the generation of a final motion compensated image; and segmenting one or more features of interest in the final motion compensated image.

According to some embodiments, a system includes an image acquisition device operative to obtain an image of an object containing movable anatomical features, the image having an image volume; a segmentation module; and a memory in communication with the image acquisition device and storing program instructions, the segmentation module operative with the program instructions to perform the functions as follows: determining one or more image locations at which motion occurred within the image volume; estimating motion at each of the one or more image locations; correcting one or more motion artifacts in the image volume at each of the one or more image locations where motion was estimated, resulting in the generation of a final motion compensated image; and segmenting one or more features of interest in the final motion compensated image.

A technical effect of some embodiments of the invention is an improved technique and system for correcting motion artifacts in images. With this and other advantages and features that will become hereinafter apparent, a more complete understanding of the nature of the invention can be obtained by referring to the following detailed description and to the drawings appended hereto.

Other embodiments are associated with systems and/or computer-readable medium storing instructions to perform any of the methods described herein.

DRAWINGS

Figure 4A:
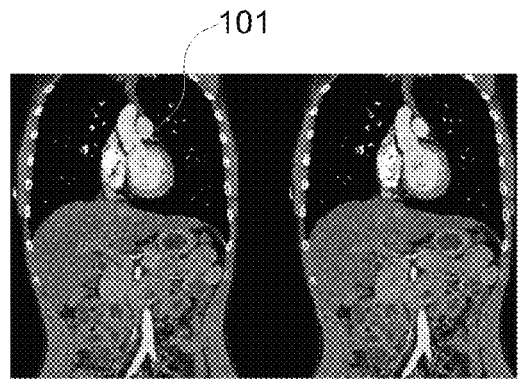
Figure 4B:
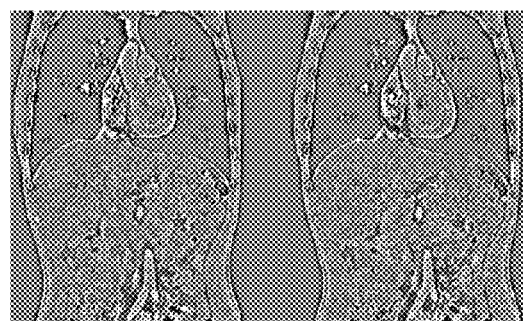
Figure 4C:

FIGS. 4A-C illustrate images according to some embodiments.

FIGS. 5A-D illustrate images according to some embodiments.

FIGS. 6A-D illustrate images according to some embodiments.

Figure 7:
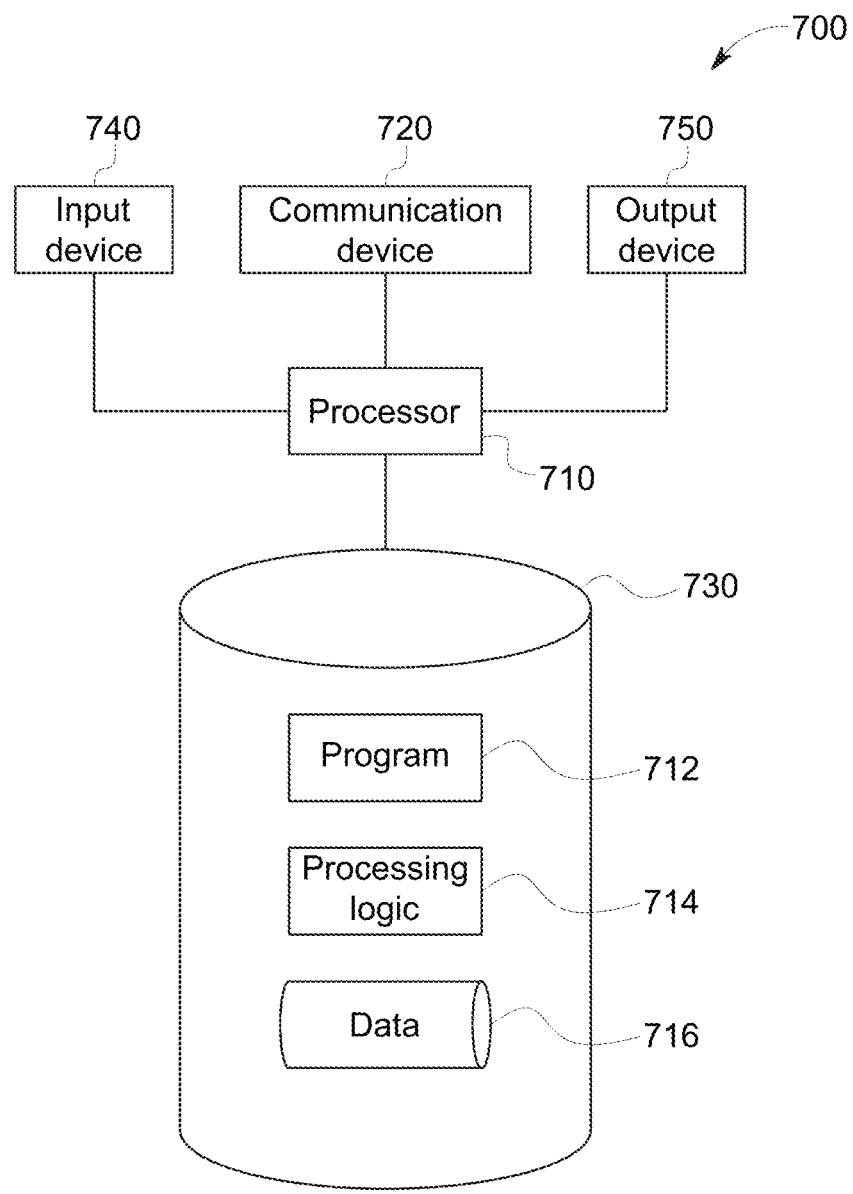

FIG. 7 illustrates s a block diagram of a system according to some embodiments.

DETAILED DESCRIPTION

Computed Tomography (CT) is a non-invasive imaging technique that can be used to visualize small structures (e.g., vessels, lung nodules, liver lesions, etc.). CT uses a CT scanner to produce detailed images of both blood vessels and tissues in various parts of the body. The images may be used by physicians to diagnose and evaluate many diseases of blood vessels and related conditions, including but not limited to, injury, aneurysms, blockages (including those from blood clots or plaques), disorganized blood vessel and blood supply to tumors, and congenital abnormalities of the heart, blood vessels or various parts of the bodies which might be supplied by abnormal blood vessels.

One of the challenges in CT is that the image features move during data acquisition. Since most image reconstruction techniques do not account for this motion, the resulting image includes image artifacts. These image artifacts may often severely distort small features, making segmentation tasks such as vessel detection and vessel tracking challenging. It is often important to track the features in such image volumes to provide advanced visualizations and to present the data that is most clinically relevant. For example, doctors may want to scan through the lumen view or navigate along the length of a particular artery to look for disease. Also, it may be important to track and segment the feature in an image in order to enable computation fluid dynamics simulations of blood flow in the feature. Poor image quality due to motion may otherwise cause such simulations to be inaccurate. The inventors note that it may be much easier to track the feature if the images are not corrupted by motion artifacts. Embodiments of the invention may correct motion artifacts prior to vessel tracking to provide a motion-free image so as to enable advanced vessel tracking and segmentation.

Conventional motion estimation compensation methods (e.g., non-rigid registration, optical flow, MAM, etc.) may require detecting/segmenting features in the image as an input for the correction in order to focus the motion estimation effort near the features of interest. These conventional methods may also require segmentation of the image as a first step for motion compensation, whereby a first step is to identify certain anatomical boundaries or landmarks in the image and subdivide the image into pieces. Embodiments described herein, on the other hand, occur prior to the detection/segmentation of the features.

Further, these conventional methods may simply warp the image (e.g., by registering a series of images together) as opposed to correcting the image. For example, a camera may take three pictures of a fast moving object, and each of the three image is blurry. Conventional methods may shift (or warp, if the process is non-rigid) these three images such that the three blurry images are superimposed on each other, so that there is no apparent motion of the object as the three frames are viewed in series. In embodiments described herein, on the other hand, the blur is actually being removed from the image to provide an image that is motion artifact free. Also, conventional methods that do correct motion within an individual image volume may require access to and use of the projection data in order to accomplish motion correction, since motion correction is traditionally done as part of the reconstruction process.

As used herein, "segmenting" means identifying or detecting the position/boundary surfaces of a particular feature in an image volume. As used herein, the terms "segmenting," "detecting" and "tracking" may be used interchangeably.

While examples used in descriptions of embodiments of the invention may be described with respect to an artery, any suitable moving anatomical feature (e.g., lung nodules, vessel boundaries, any organ etc.) may be used.

Some embodiments provide a method and system for executing a motion correction that prior to vessel detection, tracking and segmentation, may first identify locations in an image where motion is occurring at which correction may be applied. The system and method may then apply an image correction to correct the motion, and thereafter may generate a motion-free volumetric image. A benefit gained from a motion-free image volume may be that it provides for more accurate segmentation of the anatomical feature. Anatomical feature detection and tracking may be determined from the resulting motion-free volumetric image.

Advantages of embodiments are that there may be a great reduction of motion artifacts in images, which may enable better vessel tracking and segmentation. Vessel tracking and segmentation may be critical to advanced applications and visualizations as well as additional processing steps that may improve the diagnostic power of CT exams in addition to other imaging exams (e.g., Magnetic Resonance Imaging (MRI) exams).

Another advantage of embodiments may be that motion compensation can be done without the original projection images, which may not be available on an image processing workstation where segmentation-type processing may typically occur. Conventionally, the image is transmitted to other devices, where it is stored, at which point it may not be motion corrected by traditional means. Conventional motion compensation techniques may be performed as part of the reconstruction, so they may require access to the original projection data.

Another advantage of embodiments may be the determination as to whether the generated image requires motion correction as described by embodiments herein, or whether a more extensive motion correction is required, if the number of motion artifacts (or magnitude of the estimated motion) is greater than a threshold value.

Figure 1:
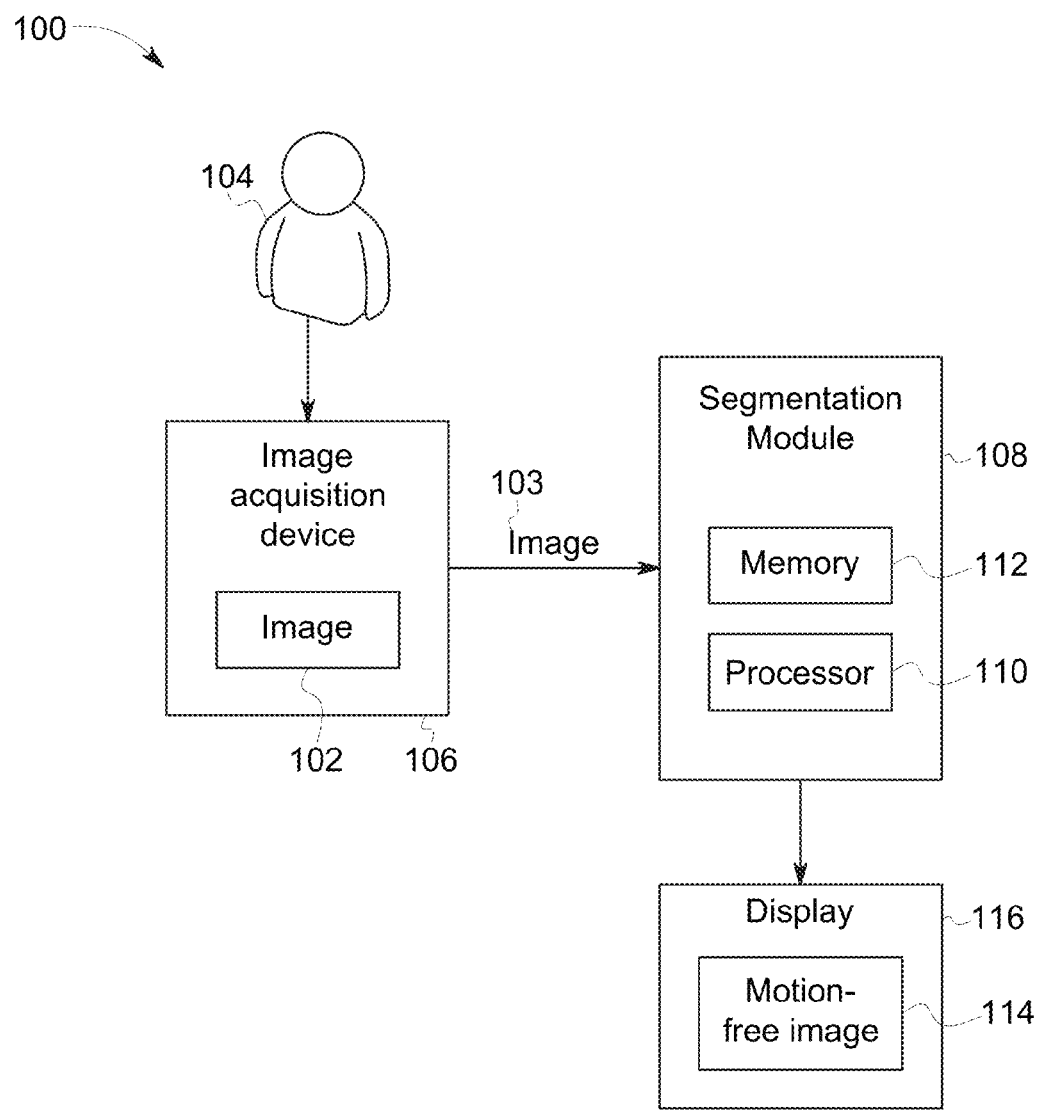
FIG. 1 illustrates a system according to some embodiments.
Figure 2:
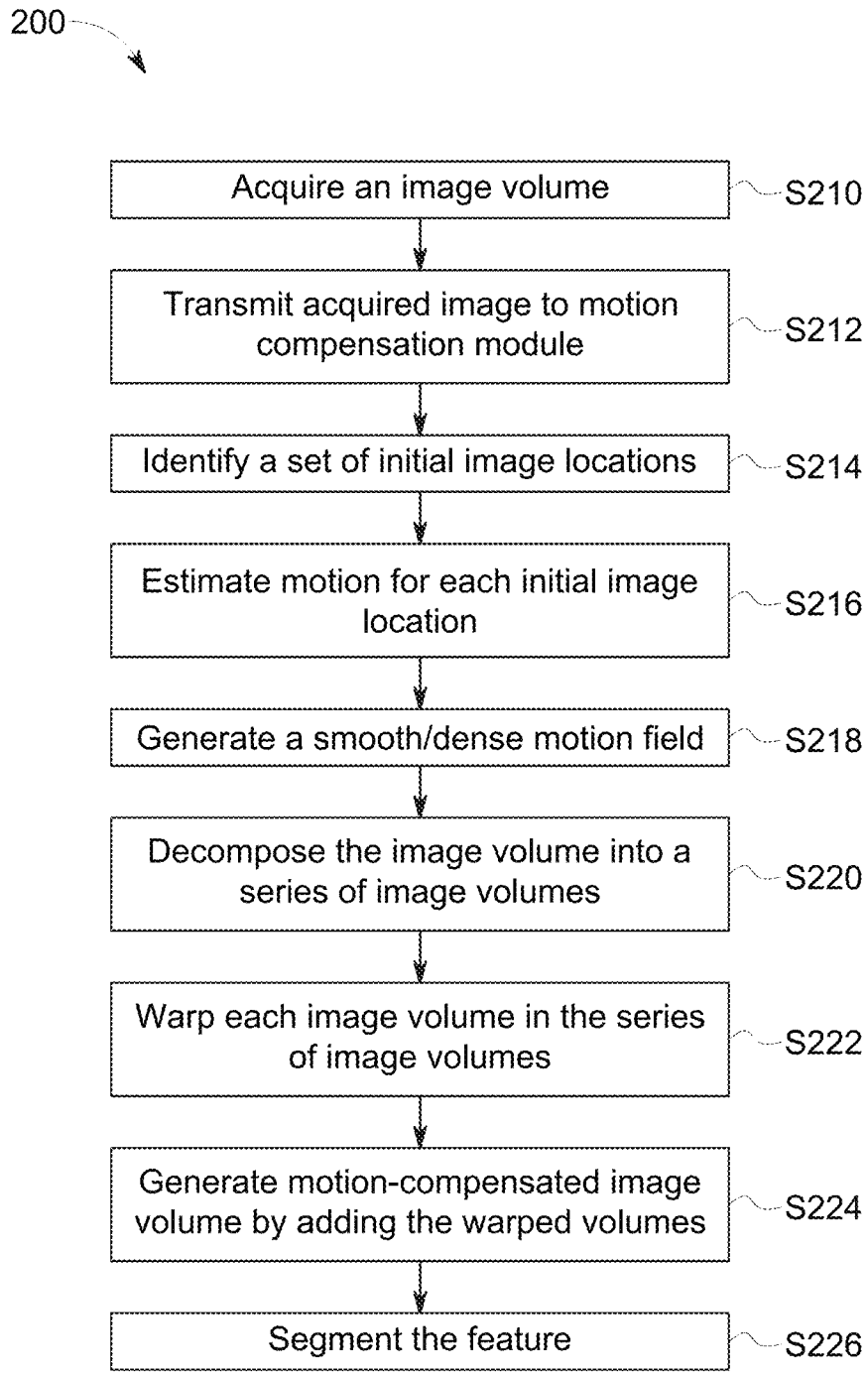
FIG. 2 illustrates a flow diagram according to some embodiments.
Figure 3:
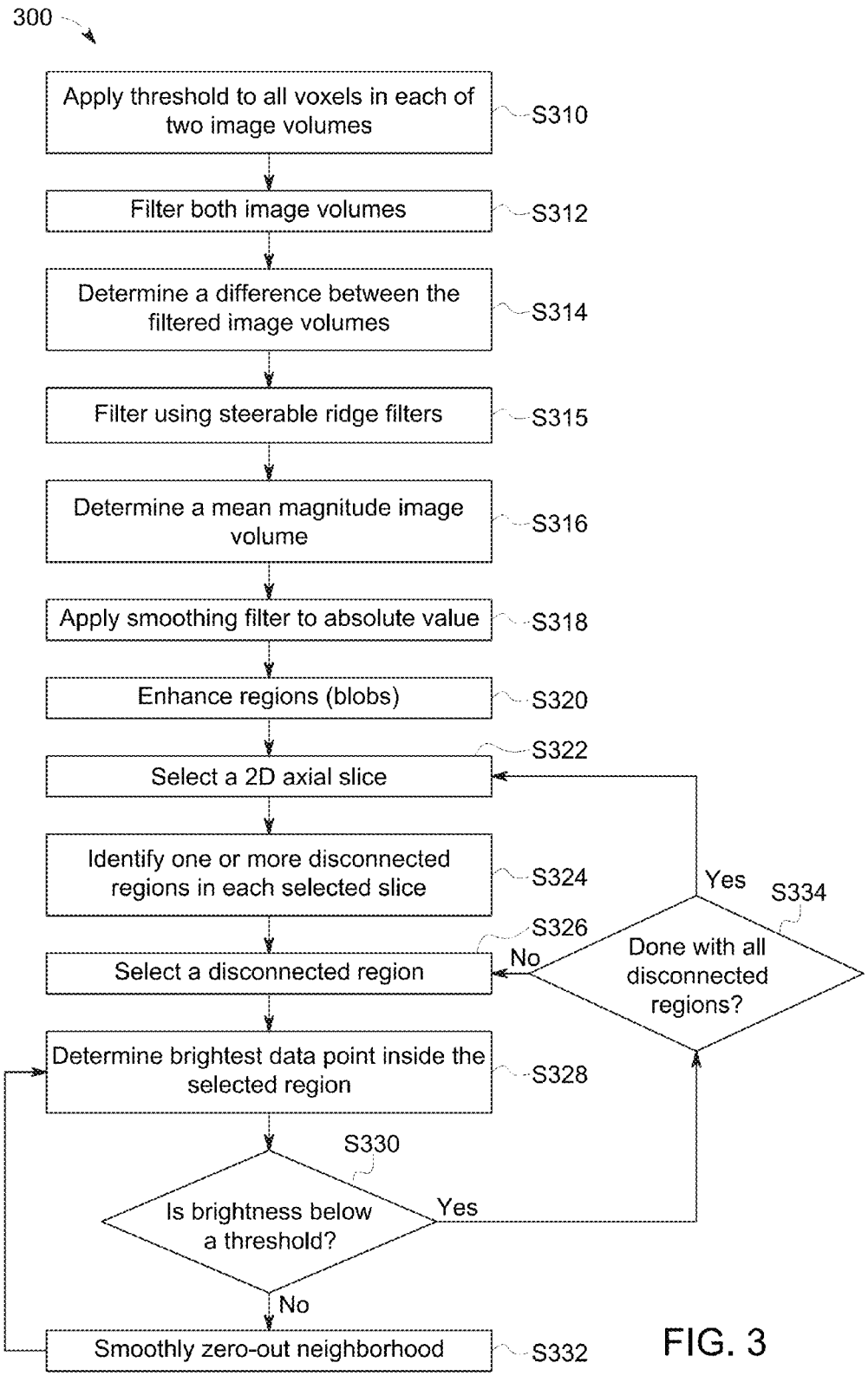
FIG. 3 illustrates a flow diagram according to some embodiments.

Turning to FIGS. 1-3, a system 100 and flow diagrams of an example of operation according to some embodiments is provided. In particular, FIGS. 2 and 3 provide a flow diagram of a process 200 and 300 respectively, according to some embodiments. Processes 200/300 and other processes described herein may be performed using any suitable combination of hardware (e.g., circuit(s)), software or manual means. In one or more embodiments, the system 100 is conditioned to perform the processes 200/300 such that the system is a special-purpose element configured to perform operations not performable by a general-purpose computer or device. Software embodying these processes may be stored by any non-transitory tangible medium including a fixed disk, a floppy disk, a CD, a DVD, a Flash drive, or a magnetic tape. Examples of these processes will be described below with respect to embodiments of the system, but embodiments are not limited thereto.

Initially, at S210, a set of two or more volumetric images (or image volumes) 102 of an anatomical feature of interest of a patient 104 is acquired with an image acquisition device 106. In some embodiments, the set of images may be reconstructed from projection datasets that are shifted in time. Each image volume 102 may consist of voxels stacked in three dimensions (3D) (e.g., a 3D volumetric image). As used herein, "image volume," "volumetric image," and "image" may be used interchangeably. Typically, as the image acquisition device 106 rotates about the patient 104, it takes projection images (or projection data) from different angles. The image acquisition device 106 may generate two image volumes—a first- (or left-) phase image volume as the image acquisition device 106 rotates from the starting position to the half-way mark, and a second- (or right-) phase image volume as the image acquisition device 106 rotates from the half-way mark to the starting position. In other words, the set of projection data used to generate the first image volume is shifted in time with respect to the set of projection data used to generate the second image volume, such that the two image volumes are generated based on projection data that is slightly shifted in time. The inventors note that left- and right-phase image volumes $I^{Left}_{x,y,z}$ and $I^{Right}_{x,y,z}$, respectively, (which may contain "clean data" corresponding to conjugate-views for a certain angular range) may be the same if there is no motion (except for typical noise) and may not be similar (ignoring changes in contrast) wherever there is motion. As such, in one or more embodiments, taking a difference of the image-volumes corresponding to these two phases may highlight regions where there is motion. As described above, the images of these features of interest may be acquired while the features of interest are in motion. Images taken while features of interest are in motion may include one or more motion artifacts 101 (FIGS. 4A and 4C) that may corrupt the image and make feature detection difficult. Other image volumes may also be generated from the acquired data. For example, a "center" phase image may use data from the center of the temporal acquisition window.

The image acquisition device 106 may be a CT scanner, an MRI scanner, or any other suitable image acquisition device. The anatomical feature of interest may be blood vessels and the organs supplied by them in various parts of the body, including but not limited to, the brain, neck, heart, chest (e.g., lungs), abdomen (e.g., kidneys and liver), pelvis, legs and feet, arms and hands.

Then in S212, the image acquisition device 106 transmits the acquired images 102 to a segmentation module 108, as indicated by directional arrow 103. The segmentation module 108 may include one or more processing elements 110 and a memory 112. The processor 110 may, for example, be a conventional microprocessor, and may operate to control the overall functioning of the segmentation module 108. In one or more embodiments, the segmentation module 108 may include a communication controller for allowing the processor 110, and hence the segmentation module 108, to engage in communication over data networks with other devices (e.g., the image acquisition device 106.) In one or more embodiments, the segmentation module 108 may include one or more memory and/or data storage devices 112, which may comprise any combination of one or more of a hard disk drive, RAM (random access memory), ROM (read only memory), flash memory, etc. The memory/data storage devices 112 may store software that programs the processor 110 and the segmentation module 108 to perform functionality as described herein.

The segmentation module 108 first identifies a set of initial image locations, $S_{Ini}$, in the image volume where motion is occurring and for which the motion compensation may be performed, in S214, as described in more detail below with respect to FIG. 3.

Then in S216 motion may be estimated at each initial image location in the set of initial image locations. In one or more embodiments, the motion at each initial image location may be estimated using a cross-correlation technique, a registration technique or a data consistency condition technique. Other suitable comparison techniques may be used.

A smooth/dense motion field is generated in S218 from the discrete set of locations at which motion was estimated. As used herein, a motion field may be a motion path for every voxel in the image volume. In one or more embodiments, the smooth/dense motion field may be generated by interpolation or extrapolation by taking the weighted average of motion for nearby (e.g., all locations within a 2-2.5 cm radius, with more weight being given to closer locations) locations that have a known motion. A determination of "nearby" locations may depend on the application. The generation of the smooth/dense motion field allows the motion to be corrected for the entire image volume.

The image volume is then decomposed in S220 into a series of image volumes that may sum to one of the original image volumes (e.g., the center phase one). In some embodiments, the decomposition may be based on a time or an angle at which the relevant data was acquired. The decomposition may be via a "partial angle back projection" process, for example. Other suitable decomposition processes may be used. In some embodiments, a series of wedge-shaped filters may be applied to the image volume, resulting in a series of image volumes, each of which represents the projection data acquired within a small period of time. This may be done without access to the projection data due to the well-known linkage between the Fourier domain and the projection domain (i.e., the central slice theorem).

Then in S222 each image volume (a 3D array of voxels) in the series of image volumes may be warped according to the motion estimated in S216 at the corresponding time or angle. In some embodiments, the motion fields determined in S218 may indicate how to warp the image volumes. In some embodiments, the warping of each image volume in the series may occur prior to adding each of the image volumes together to form the motion-free image. In one or more embodiments, as used herein a motion path describes the position of a voxel as a function of time, and to warp an image, each voxel in the image corresponding to time t is replaced by the value within the pre-warped image volume that corresponds to the position of the given voxel at the given time, according to the motion field. For example, if a certain voxel, located at position (x,y,z) is moving only along the x direction according to the following motion path:

| x − 5 | x − 4 | x − 3 . . . x . . . x + 3 | x + 4 | x + 5 |
|---|---|---|---|---|
| $t_1$ | $t_2$ | $t_3$ | | $t_{11}$ | then for the frame corresponding to time ti, we would assign the selected voxel the intensity value of the pre-warped image at (x−5,y,z). Similarly, for $t_{11}$, we would warp the image 5 mm to the left near the considered voxel. The movement may not be linear in time and may not be constrained to a single dimension (e.g., right, left, in, out, up, down).

Then at S224 the segmentation module 108 generates a final motion-compensated image segmentation 114 ("image segmentation") by adding together each of the warped image volumes to produce the compensated volume. In one or more embodiments, the image segmentation 114 may be used for detection/segmentation of anatomical features in S226, resulting in a more accurate detection/segmentation than would have been possible without motion compensation.

Turning to FIG. 3, a process 300 for identifying a set of initial image locations, $S_{Ini}$, in the image volume where motion is occurring and for which the motion compensation may be performed is provided.

In S310 a threshold may be applied to all voxels in the selected left- and right-phase image volumes $I^{Left}_{x,y,z}$ and $I^{Right}_{x,y,z}$, (FIG. 4A) such that all voxels below a particular HU, (e.g., 700 HU), are set to a pre-defined HU (e.g., 700 HU) to remove spurious structures, and may be referred to as "intensity clipping". Then in S312, both image volumes are filtered. A difference between the filtered image volumes is determined in S314. In some embodiments a 2D high-pass filter (HPF) may be applied in S312 to the axial slices of $I^{Left}_{x,y,z}$ and $I^{Right}_{x,y,z}$, (FIG. 4B) to respectively obtain $I^{Left}_{x,y,z}$ and $I^{Right}_{x,y,z}$ such that low-frequency contrast-difference may not dominate changes due to motion in the difference-volume $I^{Diff}_{x,y,z} = I^{Left\_HPF}_{x,y,z} - I^{Right\_HPF}_{x,y,z}$. As such, in some embodiments $I^{Diff}_{x,y,z}$ (FIG. 5A) may indicate motion-corrupted regions 101.

Then $I^{Diff}_{x,y,z}$ may be filtered in S315 using one or more steerable-ridge-filters to obtain filtered images that may highlight structures oriented along specific directions. In one or more embodiments, the set of steerable-ridge-filters may preferentially keep frequency components that fall within a narrow angular range. In S316, a mean of the absolute value across each element in the one or more filtered-responses of $I^{Diff}_{x,y,z}$ to the ridge-filters, denoted by $I^{Abs}_{x,y,z}$, is determined (e.g., to produce a mean absolute value volume) as shown, for example, in FIG. 5B. Of note, the black and white in FIGS. 5B, 5C, 5D, 6A, 6B and 6C, are displayed on an inverted color scheme, such that white is "smaller" value and darker is the "larger" value.

Figure 5A:
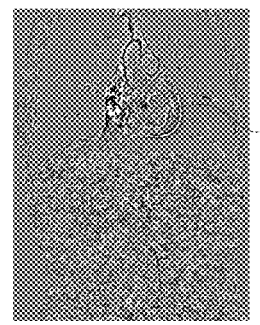
Figure 5B:
Figure 5C:
Figure 5D:
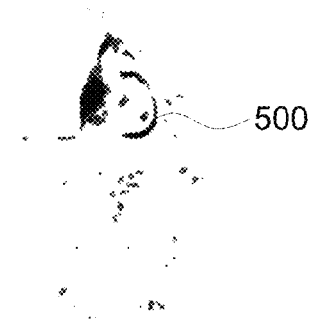

In some embodiments, the mean magnitude absolute image volume $I^{Abs}_{x,y,z}$ may indicate areas or regions 500 that are changing due to motion (e.g., highlighted by the darker shades in FIGS. 5B, 5C and 5D). The inventors note that the motion areas/regions 500 are dark in FIGS. 5 and 6, as the color scale has been inverted. However, in embodiments, the areas/regions 500 may be bright compared to the background on a normal gray-scale color scheme.

The mean magnitude absolute image volume $I^{Abs}_{x,y,z}$ is smoothed in S318 to reduce the effect of noise to produce $I^{Abs\_Smooth}_{x,y,z}$ (FIG. 5C). The mean magnitude absolute image volume $I^{Abs}_{x,y,z}$ may be smoothed via application of a 3D Gaussian smoothing filter or any other suitable smoothing filter. In some embodiments the smoothed mean magnitude absolute image volume $I^{Abs\_Smooth}_{x,y,z}$ may contain blobs 500 (e.g., dark blobs in FIG. 5C).

The inventors note that motion-corrupted regions distributed within $I^{Abs\_Smooth}_{x,y,z}$ may be sparse and the rest of the regions in $I^{Abs\_smooth}_{x,y,z}$ may be deemed as background. In some embodiments $I^{Abs\_Smooth}_{x,y,z}$ may be thresholded with the threshold-value set to $T_{background}$, which is determined based on the histogram of $I^{Abs\_Smooth}_{x,y,z}$, to obtain $I^{Abs\_Thresh}_{x,y,z}$ (FIG. 5D).

The blobs 500 in $I^{Abs\_Thresh}_{x,y,z}$ may be further enhanced in S320. In one or more embodiments to enhance the blobs 500, $I^{Abs\_Thresh}_{x,y,z}$ may be filtered with circular annuli-filters and then the positive component of the filtered responses may be averaged to yield $I^{Abs\_Filt}_{x,y,z}$ (FIG. 6A). Then, to further enhance regions 500 where there is possible motion (e.g., blobs), take the ratio $I^{Abs\_Filt}_{x,y,z} / I^{Abs\_Thresh}_{x,y,z}$ and retain only those voxels where $I^{Abs\_Thresh}_{x,y,z} > 0$ resulting in $I^{Motion\_Regions}_{x,y,z}$. For example, FIG. 6B shows the ratio of the images in FIGS. 6A and 5D. In some embodiments, determining $I^{Abs\_Thresh}_{x,y,z} > 0$ may avoid producing "infinities" in any of the image volumes produced further along the process chain.

In some embodiments, bright features in $I^{Motion\_Regions}_{x,y,z}$ may be indicative of regions corrupted by motion (e.g., where motion is occurring). In some embodiments $I^{Motion\_Regions}_{x,y,z}$ may be sliced into one or more axial-slices (FIG. 6C), wherein the axial slices may be native to the reconstruction geometry. In S322, an axial slice is selected. In S324, one or more disconnected regions 600 (e.g., FIGS. 6C) are identified in each slice of $I^{Motion\_Regions}_{x,y,z}$. Then in S326 a disconnected region is selected, and a brightest point 602 (FIG. 4C) inside the selected disconnected region is determined in S328. For each determined brightest point 602, the corresponding image location is stored in memory 112. Later, motion will be estimated at each of these image locations. In S330 it is determined whether the brightness of the brightest point is below a threshold value found using a histogram of voxels in the disconnected region.

If the brightness is not below the threshold value, the process proceeds to S332, where a neighborhood around the brightest point is smoothly zeroed-out. Care is taken to avoid finding bright-points too close to each other by smoothly zeroing-out a neighborhood in $I^{Motion\_Regions}_{x,y,z}$ (e.g., by a few millimeters) around a previous selected point in S332; this operation allows for the sequential identification of the next brightest point at least a few millimeters away from the previously selected brightest point. In some embodiments, smoothly zeroing-out the neighborhood around the brightest point may precede determining the next brightest point. In one or more embodiments it may be desirable to ensure that the identified image locations are spaced apart to expedite the motion estimation, such that the bright points in each disconnected region are well-distributed. In one or more embodiments, taking a product of $I^{Motion\_Regions}_{x,y,z}$ at a selected location with a 2D dimple function (FIG. 6D, not on the same scale as FIGS. 6A, 6B and 6C) may smoothly zero-out the image volume $I^{Motion\_Regions}_{x,y,z}$ in a neighborhood around the selected location. Of note, unlike the images in FIGS. 5B-6C, the image in FIG. 6D is not in an inverted scale. The 2D dimple function may be a radially symmetric function that is zero at the center and smoothly increase radially outward to unity (FIG. 6D).

In one or more embodiments, S328 through 332 may be repeated to determine sequential brightest image locations until the maximum brightness of the non-zeroed-out regions falls below a threshold. If in S330 it is determined the brightness is below the threshold value, the process proceeds to S334, where it is determined whether each of the disconnected regions have been searched for points brighter than a fixed threshold. If disconnected regions remain to be searched for points, the process returns to S326 to select the next disconnected region. If all disconnected regions have been searched for points brighter than a fixed threshold, the process returns to S322 to select a next 2D axial slice. The determined image locations for each of the disconnected regions in each of the 2D axial slices may be combined to form a combined set of initial image locations for the whole image volume. In one or more embodiments, each disconnected region 600 may be considered separately, and initial image locations may be identified in each region 600 individually on a region-by-region basis such that all regions indicative of motion may be analyzed, regardless of their size.

In one or more embodiments, S322 through 332 may be applied on sagittal slices or on coronal slices or on slices oriented along arbitrary directions of the image volume $I^{Motion\_Regions}_{x,y,z}$ as may be beneficial to the process of finding bright points S328 and smoothly zeroing out their neighborhoods S332.

Note the embodiments described herein may be implemented using any number of different hardware configurations. For example, FIG. 7 illustrates a segmentation processing platform 700 that may be, for example, associated with the system 100 of FIG. 1. The segmentation processing platform 700 comprises a segmentation platform processor 710 ("processor"), such as one or more commercially available Central Processing Units (CPUs) in the form of one-chip microprocessors, coupled to a communication device 720 configured to communicate via a communication network (not shown in FIG. 7). The communication device 720 may be used to communicate, for example, with one or more users. The segmentation processing platform 700 further includes an input device 740 (e.g., a mouse and/or keyboard to enter information about the measurements and/or assets) and an output device 750 (e.g., to output and display the data and/or recommendations).

The processor 710 also communicates with a memory/storage device 730. The storage device 730 may comprise any appropriate information storage device, including combinations of magnetic storage devices (e.g., a hard disk drive), optical storage devices, mobile telephones, and/or semiconductor memory devices. The storage device 730 may store a program 712 and/or segmentation processing logic 714 for controlling the processor 710. The processor 710 performs instructions of the programs 712, 714, and thereby operates in accordance with any of the embodiments described herein. For example, the processor 710 may receive image volume data and then may apply the segmentation module 108 via the instructions of the programs 712, 714 to generate a motion-free image segmentation 114 ("image segmentation").

The programs 712, 714 may be stored in a compressed, uncompiled and/or encrypted format. The programs 712, 714 may furthermore include other program elements, such as an operating system, a database management system, and/or device drivers used by the processor 710 to interface with peripheral devices.

As used herein, information may be "received" by or "transmitted" to, for example: (i) the platform 700 from another device; or (ii) a software application or module within the platform 700 from another software application, module, or any other source.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein; by way of example and not limitation, an analyzer module. The method steps can then be carried out using the distinct software modules and/or sub-modules of the system, as described above, executing on one or more hardware processors 710 (FIG. 7). Further, a computer program product can include a computer-readable storage medium with code adapted to be implemented to carry out one or more method steps described herein, including the provision of the system with the distinct software modules.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

The invention claimed is:

1. A method comprising:
    determining one or more image locations at which motion occurred within an image volume of an object containing movable anatomical features prior to segmenting the movable anatomical features;
    estimating motion at each of the one or more image locations;
    generating a smooth motion field from the estimated motion at the one or more image locations at which motion was estimated;
    decomposing the image volume into a series of two or more image volumes that sum to the original image volume;
    correcting one or more motion artifacts in the image volume at each of the one or more image locations, where motion was estimated resulting in the generation of a final motion compensated image; and
    segmenting one or more features of interest in the final motion compensated image.

2. The method of claim 1, further comprising:
    obtaining at least two image volumes prior to determining one or more image locations at which motion occurred.

3. The method of claim 1, wherein decomposing is based on one of a time at which the projection data were acquired or an angle at which the projection data were acquired.

4. The method of claim 3, further comprising:
    warping each image volume in the series of two or more image volumes according to the motion estimate at the corresponding time or angle at which the projection data that contributed to each volume were acquired.

5. The method of claim 4, wherein correcting one or more motion artifacts in the image volume further comprises:
    summing the two or more warped image volumes in the series.

6. The method of claim 1, wherein each image volume in the series of two or more image volumes represents a snapshot in time.

7. The method of claim 1, wherein determining one or more image locations at which motion occurred within an image volume further comprises:
    selecting two image volumes from a set of acquired image volumes;
    determining a difference between the two image volumes; and
    filtering the difference between the two image volumes with one or more steerable ridge filters to generate one or more filtered image volumes.

8. The method of claim 7, further comprising:
    determining a mean absolute value across each element in the one or more filtered image volumes to produce a mean absolute value volume, wherein the mean absolute value volume highlights one or more areas in the one or more filtered image volumes where motion is occurring; and
    applying a smoothing filter to the mean absolute value volume to generate a smoothed absolute value image volume.

9. The method of claim 8, further comprising:
    identifying one or more image locations distributed within each of the one or more areas in the smoothed absolute value image volume where motion is occurring.

10. The method of claim 9, wherein the one or more image locations are identified by:
    slicing the image volume into one or more slices;
    identifying one or more disconnected regions in each slice;
    determining the locations corresponding to a well-distributed set of bright points in each disconnected region.

11. A system comprising:
    an image acquisition device operative to obtain an image of a movable anatomical feature, the image having an image volume;
    a segmentation module; and
    a memory in communication with the image acquisition device and storing program instructions, the segmentation module operative with the program instructions to perform the functions as follows:
        determining one or more image locations at which motion occurred within the image volume;
        estimating motion at each of the one or more image locations;

correcting one or more motion artifacts in the image volume at each of the one or more image locations where motion was estimated, resulting in the generation of a final motion compensated image volume; and segmenting one or more features of interest in the final motion compensated image, wherein a smooth motion field is generated, via the segmentation module, from the one or more image locations at which motion was estimated; and wherein the image volume is decomposed, via the segmentation module, into a series of two or more image volumes that sum to the original image volume.

12. The system of claim 11, wherein decomposing is based on one of a time at which the relevant projection data were acquired or an angle at which the relevant projection data were acquired.

13. The system of claim 12, wherein each image volume in the series of two or more image volumes is warped according to the motion estimate at the corresponding time or angle at which the relevant projection data were acquired.

14. The system of claim 13, wherein the two or more warped image volumes in the series are summed to correct one or more motion artifacts in the image volume.

15. The system of claim 11, wherein the segmentation module is further operative to determine one or more image locations at which motion occurred within an image volume by:

selecting two image volumes from a set of acquired image volumes;

determining a difference between the two image volumes;

filtering the difference between the two image volumes with one or more steerable ridge filters to generate one or more filtered image volumes.

16. The system of claim 15, wherein the segmentation module is further operative to:

determine a mean absolute value across each element in the one or more filtered image volumes to produce a mean absolute value volume, wherein the mean absolute value volume highlights one or more areas in the filtered image volumes where motion is occurring; and apply a smoothing filter to the mean absolute value volume to generate a smoothed absolute value image volume.

17. The system of claim 16, wherein the segmentation module is further operative to:

identify one or more image locations distributed within each of the one or more areas in the smoothed absolute value image volume where motion is occurring.

18. The system of claim 17, wherein the segmentation module is further operative to identify the one or more image locations by:

slicing the image volume into one or more slices;

identifying one or more disconnected regions in each slice;

determining the locations corresponding to a well-distributed set of bright points in each disconnected region.

* * * * *